United States Patent
Sakai et al.

(10) Patent No.: US 11,456,115 B2
(45) Date of Patent: Sep. 27, 2022

(54) ELECTRIC TRANSMISSION DEVICE IN RELATIVELY ROTATING PARTS

(71) Applicants: Kayo Sakai, Kuwana (JP); Eiichirou Shimazu, Kuwana (JP); Shougo Kanbe, Kuwana (JP)

(72) Inventors: Kayo Sakai, Kuwana (JP); Eiichirou Shimazu, Kuwana (JP); Shougo Kanbe, Kuwana (JP)

(73) Assignee: NTN CORPORATION, Osaka (JP)

( * ) Notice: Subject to any disclaimer, the term of this patent is extended or adjusted under 35 U.S.C. 154(b) by 997 days.

(21) Appl. No.: 16/180,232

(22) Filed: Nov. 5, 2018

(65) Prior Publication Data
US 2019/0103219 A1 Apr. 4, 2019

Related U.S. Application Data

(63) Continuation of application No. PCT/JP2017/017136, filed on May 1, 2017.

(30) Foreign Application Priority Data

May 11, 2016 (JP) .............................. JP2016-095206
Nov. 9, 2016 (JP) .............................. JP2016-218804

(51) Int. Cl.
*H01F 38/14* (2006.01)
*A61F 2/60* (2006.01)
(Continued)

(52) U.S. Cl.
CPC ................ *H01F 38/14* (2013.01); *A61F 2/54* (2013.01); *A61F 2/60* (2013.01); *A61H 3/00* (2013.01);
(Continued)

(58) Field of Classification Search
CPC .. H01F 38/14; H01F 38/18; A61F 2/54; A61F 2/60; A61H 3/00; A61H 2201/1215;
(Continued)

(56) References Cited

U.S. PATENT DOCUMENTS

| 8,164,925 B2 | 4/2012 | Abe et al. |
| 10,243,406 B2 | 3/2019 | Ushijima et al. |

(Continued)

FOREIGN PATENT DOCUMENTS

| CN | 1377116 A | 10/2002 |
| EP | 0680060 | 11/1995 |

(Continued)

OTHER PUBLICATIONS

International Preliminary Report on Patentability dated Nov. 22, 2018 in corresponding International Patent Application No. PCT/JP2017/017136.

(Continued)

*Primary Examiner* — Carlos Amaya

(57) ABSTRACT

Provided is an electric transmission device that is provided at relatively rotating parts of a mechanical apparatus. The electric transmission device (E) includes a pair of magnetic elements (1A, 1B) relatively rotatable about the same axis (O). The magnetic elements (1A, 1B) each includes a core (2A, 2B) and a coil (3A, 3B) having a conductive wire. One of the coil (3A) and the coil (3B) is located at an inner side of the other coil in a radial direction, and the coils (3A and 3B) are magnetically coupled to each other. Each bobbin (4A, 4B) includes a cylinder (4aA, 4aB) and a dis-shaped flange (4bA, 4bB). The flanges (4bA, 4bB) are slidably in contact with each other at contact surfaces (10a, 11a) thereof in the axial direction.

12 Claims, 10 Drawing Sheets

(51) Int. Cl.
  *H01F 38/18* (2006.01)
  *A61F 2/54* (2006.01)
  *H02K 1/28* (2006.01)
  *A61H 3/00* (2006.01)

(52) U.S. Cl.
  CPC .............. *H01F 38/18* (2013.01); *H02K 1/28* (2013.01); *A61H 2201/1215* (2013.01); *A61H 2201/164* (2013.01); *A61H 2201/165* (2013.01); *A61H 2201/1635* (2013.01)

(58) Field of Classification Search
  CPC ...... A61H 2201/1635; A61H 2201/164; A61H 2201/165; H02K 1/28
  See application file for complete search history.

(56) References Cited

U.S. PATENT DOCUMENTS

| | | |
|---|---|---|
| 2009/0295523 A1 | 12/2009 | Schwander et al. |
| 2010/0033156 A1 | 2/2010 | Abe et al. |
| 2017/0149285 A1 | 5/2017 | Ushijima et al. |
| 2019/0140492 A1* | 5/2019 | Beyer .................... H02J 50/05 |
| 2019/0214853 A1 | 7/2019 | Ushijima et al. |

FOREIGN PATENT DOCUMENTS

| | | |
|---|---|---|
| JP | 8-51041 | 2/1996 |
| JP | 11-354348 | 12/1999 |
| JP | 2003-59736 | 2/2003 |
| JP | 2006-287041 | 10/2006 |
| JP | WO2007/029438 | 3/2007 |
| JP | 2007-321895 | 12/2007 |
| JP | 2008-125198 | 5/2008 |
| JP | 2015-6266 | 1/2015 |
| JP | WO2015/173850 | 11/2015 |
| JP | 2015-216796 | 12/2015 |

OTHER PUBLICATIONS

International Search Report dated Jul. 4, 2017 in corresponding International Patent Application No. PCT/JP2017/017136.
Japanese Office Action dated Oct. 23, 2019 in corresponding Japanese Patent Application No. 2016-095206.
Chinese Office Action dated Mar. 10, 2020, in corresponding Chinese Patent Application No. 201780028737.6.

* cited by examiner

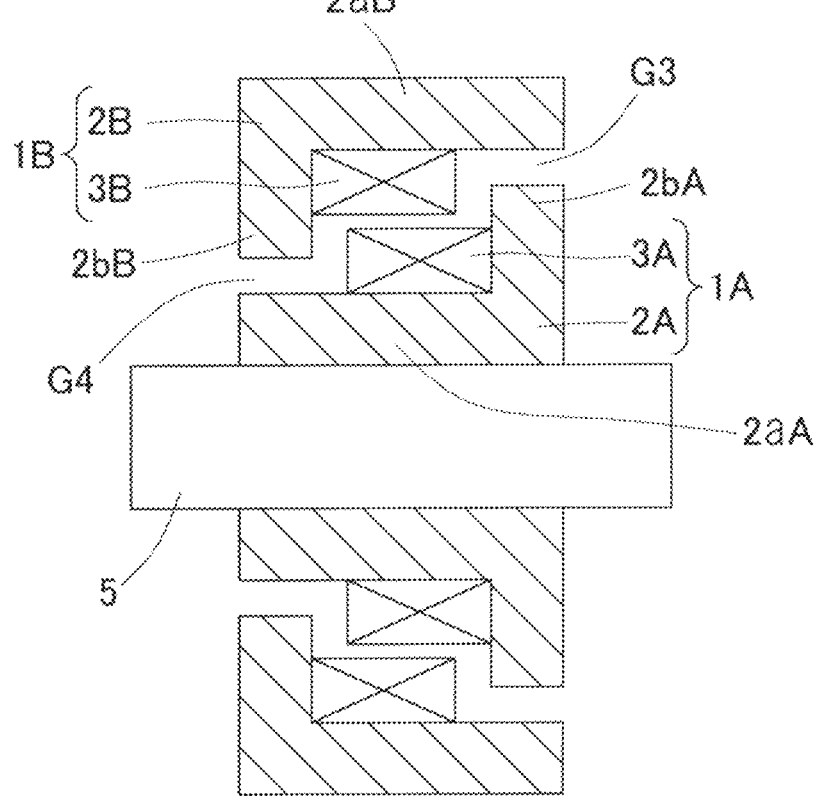

ELECTRIC TRANSMISSION DEVICE IN RELATIVELY ROTATING PARTS

CROSS REFERENCE TO THE RELATED APPLICATION

This application is a continuation application, under 35 U.S.C. § 111(a), of international application No. PCT/JP2017/017136, filed May 1, 2017, which claims based on and claims Convention priority to Japanese patent application No. 2016-095206, filed May 11, 2016, and Japanese patent application No. 2016-218804, filed Nov. 9, 2016, the entire disclosures of which are herein incorporated by reference as a part of this application.

BACKGROUND OF THE INVENTION

Field of the Invention

The present invention relates to an electric transmission device in relatively rotating parts, the electric transmission device being disposed at the relatively rotating parts in a robot, an assist suit, or another mechanical apparatus having the relatively rotating parts such as a joint. The electric transmission device is configured to transmit electric power or a signal in a non-contact manner.

Description of Related Art

A joint or rotating parts in an electric power and signal transmission path usually ensure a movable range with a loosened cable, through which electric power and/or a signal is transmitted. The cable can be bent and stretched every time when the joint or the rotating parts is actuated. The cable can be formed from copper, aluminum, or the like. Such cable may be broken by the stress that is repeatedly generated in a conductive portion thereof. The cable can also limit the movable range.

A slip ring at movable parts can replace the cable. However, the slip ring can generate abrasion powder at an electric contact. A rotary connector using a conductive liquid metal may replace the slip ring. However, such liquid metal includes mercury, which affects the environment. Such liquid metal can also increase rotary torque since a contact rubber seal is employed to prevent leak of the liquid metal.

As a solution to the above respective problems, an electric transmission device in which coils of a pair of magnetic elements capable of rotating relative to each other about the same axis are magnetically coupled to each other, has been proposed (for example, Patent Documents 1 to 3). Each magnetic element includes a core and the coil. Patent Document 1 describes a configuration in which the respective coils of a pair of magnetic elements are disposed so as to oppose each other in an axial direction. Patent Documents 2 and 3 each describe a configuration in which the respective coils of a pair of magnetic elements are disposed so as to oppose each other in a radial direction. For example, these electric transmission devices are suitably used in relatively rotating parts such as an elbow joint of an assist suit (power assist suit) as described in Patent Document 4.

RELATED DOCUMENT

Patent Document

[Patent Document 1] JP Laid-open Patent Publication No. H11-354348
[Patent Document 2] JP Laid-open Patent Publication No. H8-51041
[Patent Document 3] JP Laid-open Patent Publication No. 2003-59736
[Patent Document 4] JP Laid-open Patent Publication No. 2015-6266

SUMMARY OF THE INVENTION

Each of the above electric transmission devices based on magnetic coupling, without a cable, eliminates the risk of breaking of wire, ensures a wide movable range, minimizes abrasion. Nevertheless, the two magnetic elements can come into contact with each other during assembling or during operation, whereby there is a possibility that the core of the magnetic element will become chipped or a coating of a wire of the coil will be peeled. Each magnetic element is supported by a housing or a shaft via a bearing, and thus hardly moves in the radial direction. Therefore, the magnetic elements would hardly come into contact with each other due to movement thereof in the radial direction. However, the magnetic elements can move in the axial direction to come into contact with each other.

An object of the present invention is to provide an electric transmission device that is provided at relatively rotating parts of a mechanical apparatus and that is able to stabilize magnetic characteristics, is able to avoid damage to two magnetic elements caused by contact therebetween, and further has good assemblability.

An electric transmission device of the present invention is an electric transmission device including a pair of first and second magnetic elements relatively rotatable about the same axis. The first and second magnetic elements, each includes a core and a coil having a conductive wire, one of the coils of the first and second magnetic elements being located at an inner side of the other coil in a radial direction with respect to the axis, the coils being configured to be magnetically coupled to each other, the magnetic coupling enabling electric power and/or an electric signal to be transmitted. The first magnetic element further includes respective first and second bobbins, the first and second bobbins being located so as to be concentric with the axis. The first and second bobbins each includes a bobbin cylinder and a disk-shaped bobbin flange, the bobbin cylinder extending in an axial direction that is a direction of the axis and having an outer circumference on which the conductive wire of the corresponding coil is wound, the disk-shaped bobbin flange extending radially outward from at least an end portion of the bobbin cylinder. The bobbin flanges of the first and second bobbins are slidably in contact with each other at contact surfaces in the axial direction of the bobbin flanges, the contact surfaces opposing each other in the axial direction.

According to this configuration, connecting the coil of one magnetic element of the pair of magnetic elements to a circuit associated with a power feeder and connecting the coil of the other magnetic element to a circuit associated with a power receiver enable electric power or an electric signal to be transmitted from the power feeder to the power receiver by means of the coils, which are magnetically coupled to each other. Since one of both coils is located at the inner side of the other coil in the radial direction, the factor of the magnetic coupling between both coils is increased as compared to that in a conventional configuration in which coils of a pair of magnetic elements oppose each other in the axial direction, thereby improving that efficiency of transmission of electric power or an electric signal. Thus, the electric transmission device is prevented from increasing in size.

Since each of the coils of the first and second magnetic elements is wound on the outer circumference of the corresponding bobbin cylinder, and both bobbin flanges are slidably in contact with each other at the contact surfaces thereof in the axial direction, the first and second magnetic elements can relatively rotate about the same axis while the distance in the axial direction of the cores and the coils between the first and second magnetic elements is maintained constant. In this way, during assembling or during operation, damage to the cores and the coils of the first and second magnetic elements due to contact therebetween can be avoided. In addition, the positions of the cores and the coils between the respective magnetic elements that are kept fixed in the axial direction stabilizes the magnetic characteristics.

Winding the conductive wires of the coils of the first and second magnetic elements on the respective outer circumferences of the bobbin cylinders of the first and second bobbins which are concentric with the axis facilitates work for winding the conductive wires on the bobbins is easy. Positioning the cores and the coils by the bobbins also facilitate assembling the electric transmission device.

As the configuration in which the bobbin flanges of the respective first and second bobbins of the respective first and second magnetic elements are slidably in contact with each other, any of embodiments described below may be adopted.

In one embodiment, at both ends or one end in the axial direction of the first and second bobbins, a position of the bobbin flange of the first bobbin and a position of the bobbin flange of the second bobbin are displaced relative to each other in the axial direction, and at at least either one of both ends or the one end in the axial direction of the first and second bobbins, an annular cut is formed on a circumferential surface of the bobbin flange located at an outer side in the axial direction, a corner portion in the radial direction of the bobbin flange located at an inner side in the axial direction is engaged with the annular cut. In this embodiment, a surface of the annular cut that faces in the axial direction and a surface of the corner portion that faces in the axial direction function as the contact surfaces in the axial direction.

In one embodiment, at both ends or one end in the axial direction of the first and second bobbins, a position of the bobbin flange of the first bobbin and a position of the bobbin flange of the second bobbin are displaced relative to each other in the axial direction, and at at least either one of both ends or the one end in the axial direction of the first and second bobbins, an annular cut is formed on a circumferential surface of the bobbin flange located at an inner side in the axial direction, a corner portion in the radial direction of the bobbin flange located at an outer side in the axial direction is engaged with the annular cut. In this embodiment, a surface of the annular cut that faces in the axial direction and a surface of the corner portion that faces in the axial direction function as the contact surfaces in the axial direction.

In one embodiment, at both ends or one end in the axial direction of the first and second bobbins, a position of the bobbin flange of the first bobbin and a position of the bobbin flange of the second bobbin are displaced relative to each other in the axial direction, and at at least either one of both ends or the one end in the axial direction of the first and second bobbins, inclined surfaces that are inclined toward the radial direction and slidably in contact with each other are provided on a circumferential surface of the bobbin flange located at an outer side in the axial direction and a circumferential surface of the bobbin flange located at an inner side in the axial direction, respectively. In this embodiment, the inclined surfaces function as the respective contact surfaces in the axial direction.

In one embodiment, at both ends or one end in the axial direction of the first and second bobbins, a position of the bobbin flange of the first bobbin and a position of the bobbin flange of the second bobbin are displaced relative to each other in the axial direction, and at at least either one of both ends or the one end in the axial direction of the first and second bobbins, an inward end surface of the bobbin flange located at an outer side in the axial direction is slidably in contact with an outward end surface of the bobbin flange located at an inner side in the axial direction. In this embodiment, the inward end surface and the outward end surface function as the respective contact surfaces in the axial direction.

In any of the above configurations, the first and second magnetic elements can relatively rotate about the same axis while the distance in the axial direction of the cores and the coils between the first and second magnetic elements is maintained constant.

The first bobbin and the second bobbin each may have a contact surface in the radial direction, the contact surfaces opposing each other in the radial direction and being slidably in contact with each other. In this case, the first and second magnetic elements can relatively rotate about the same axis while the distance in the radial direction of the cores and the coils between the first and second magnetic elements is maintained constant.

The coil of the first magnetic element may be located at the inner side of the other coil in the radial direction, the core of the first magnetic element may have an L cross-sectional shape, the core of the first magnetic element including a first core cylinder and a first core flange, the first core cylinder being located on an inner side of an inner circumference of the coil of the first magnetic element, the first core flange extending radially outward from an end portion of the first core cylinder, the first core flange having a radially outer end that has a larger diameter than the coil of the second magnetic element, and the core of the second magnetic element may have a L cross-sectional shape that is symmetrical to the core of the first magnetic element, the core of the second magnetic element including a second core cylinder and a second core flange, the second core cylinder being located on the outer side of an outer circumference of the coil of the second magnetic element, the second core cylinder having an end portion that has an end surface opposing the first core flange of the core of the first magnetic element across a first gap, the second core flange extending radially inward from the other end portion of the second core cylinder, the second core flange having a radially inner end portion opposing an end surface of the first core cylinder of the core of the first magnetic element across a second gap.

Alternatively, the coil of the first magnetic element may be located at the inner side of the other coil in the radial direction, the core of the first magnetic element may have an L cross-sectional shape, the core of the first magnetic element including a first core cylinder and a first core flange, the first core cylinder being located on an inner side of an inner circumference of the coil of the first magnetic element, the first core flange extending radially outward from an end portion of the first core cylinder, the first core flange having a radially outer end portion opposing an inner circumferential surface of a core end portion of the second magnetic element across a first gap, and the core of the second magnetic element may have a L cross-sectional shape that is symmetrical to the core of the first magnetic element, the core of the second magnetic element including a second core cylinder and a second core flange, the second core cylinder being located on an outer side of an outer circumference of the coil of the second magnetic element, the second core cylinder having an end portion that has an inner circumferential surface opposing the first core flange of the core of the first magnetic element, the second core flange extending radially inward from the other end portion of the second core cylinder, the second core flange having a radially inner end that has a smaller diameter than the coil of the second magnetic element.

These magnetic elements may be regarded as including the first magnetic element having a projection shape, which is almost the same structure as a drum-shaped magnetic element without one of opposite flanges, and the second magnetic element having a recess, which is a cut shape. According to this configuration, the distance between the coils and the gaps is larger as compared to that with a pair of conventional magnetic elements having pot-shaped cores combined, and thus a leakage magnetic flux generated at the gap is less likely to be absorbed by the coil, so that magnetic energy consumed by the coil is reduced and the inductance value is improved. In addition, one of the coils associated with the respective power feeder and receiver can be disposed radially inward of the other coil, and thus the coupling factor therebetween is increased and a leakage magnetic flux can be reduced. In this way, the inductance value is improved, and the core size can be reduced further. Moreover, the first and second magnetic elements have a projection shape and a recess shape, respectively, and thus are easily distinguished, so that erroneous assembling can be prevented.

A capacitor and a leakage inductance of a leakage magnetic flux at a gap between the first and second magnetic elements may form a resonance circuit. The resonance circuit includes a coil associated with a power receiver implemented at the first or second magnetic elements and a capacitor connected to the coil. The efficiency can be improved by the resonance circuit formed by the leakage inductance of the magnetic flux leaking to the gap and the capacitor connected to the coil of the magnetic element associated with the power receiver.

The first magnetic element may be fixed to a shaft, and the second magnetic element may be mounted to the shaft through a radial rolling bearing. In the case of this configuration, the pair of magnetic elements can be supported by the shaft and the radial rolling bearing so as to be rotatable relative to each other in this electric transmission device alone, thereby facilitating assembling the electric transmission device to the mechanical apparatus.

The first magnetic element may be mounted on one component in a pair of relatively bending components and the second magnetic element may be mounted on the other component in the pair. The pair forms a joint of a mechanical apparatus. The effects of the electric transmission devices according to the respective embodiments will be sufficiently exhibited in the joint of the mechanical apparatus.

The mechanical apparatus may be a power assist suit that is worn on a human body and assists movement of an arm, a hand, a leg, or a foot of the human body with a drive source. For the power assist suit, reliability in transmission and size reduction are strongly desired. Meanwhile, the electric transmission device according to each embodiment has reliability in transmission and a reduction in the size thereof is easily achieved, and thus the electric transmission device can sufficiently meet these desires.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 15 is a longitudinal sectional view of the electric transmission device in relatively rotating parts according to the first to fifth embodiments of the present invention, wherein the configuration of a core is shown in detail;

DESCRIPTION OF EMBODIMENTS

Figure 1:
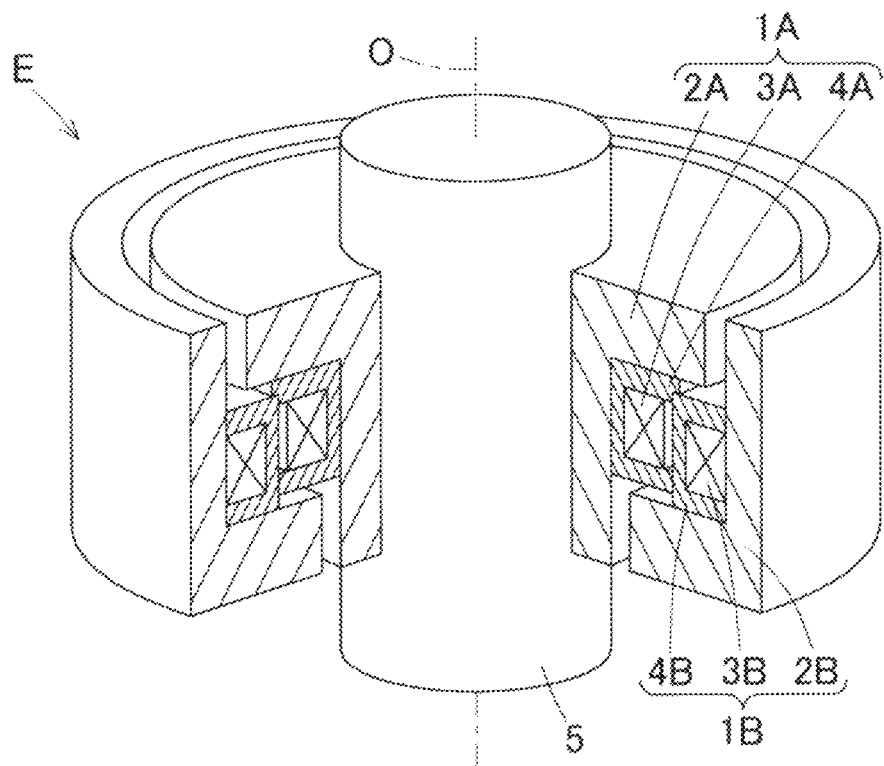
FIG. 1 is a partially cutaway perspective view illustrating an electric transmission device in relatively rotating parts according to a first embodiment of the present invention.
Figure 2:
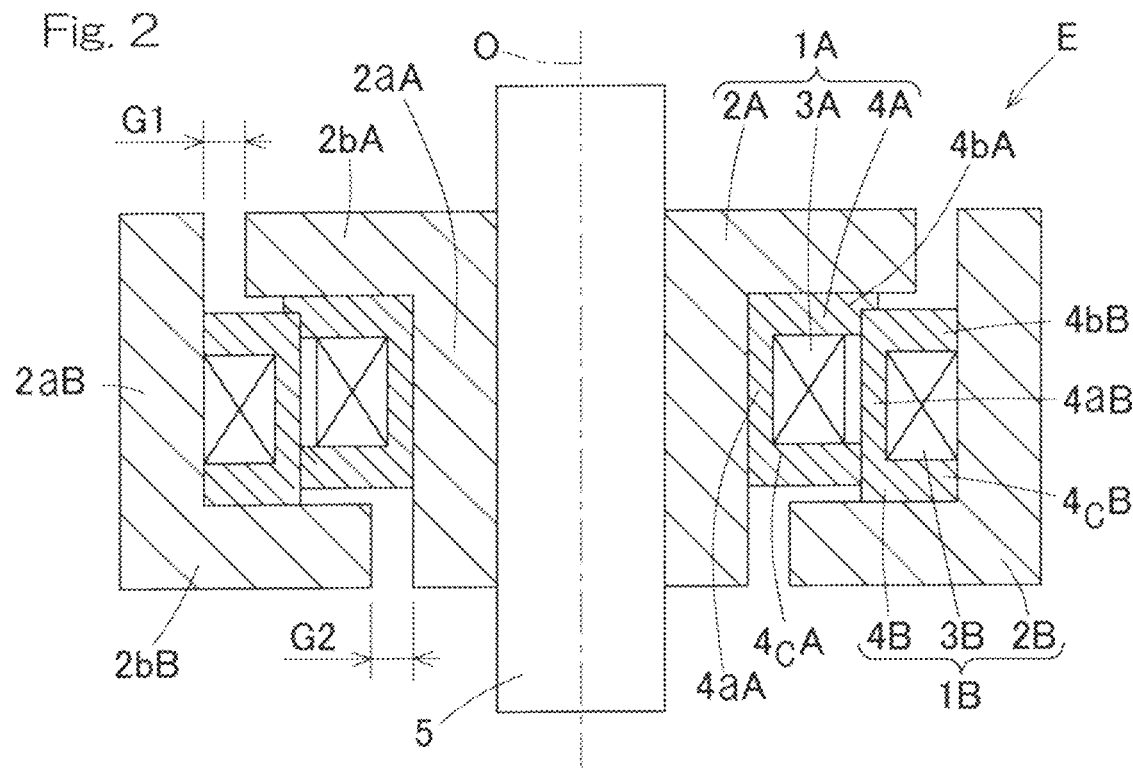
FIG. 2 is a longitudinal sectional view of the electric transmission device in FIG. 1.

An embodiment of the present invention will be described with reference to FIG. 1 to FIG. 3. FIG. 1 is a partially cutaway perspective view of an electric transmission device according to a first embodiment, in which the electric transmission device is assembled to a shaft. FIG. 2 is a longitudinal sectional view of the electric transmission device. The electric transmission device E is configured to be provided at relatively rotating parts of a mechanical apparatus such as a later-described assist suit. The electric transmission device E is related to a transformer. The device includes a pair of first and second magnetic elements 1A and 1B capable of rotating relative to each other about the same axis O. These first and second magnetic elements 1A and 1B each include a core 2A (2B), a coil 3A (3B), and a bobbin 4A (4B). The coils 3A and 3B of both magnetic elements 1A and 1B are located at the inner and outer sides in a radial direction, respectively, and are magnetically coupled to each other. The magnetic coupling enables electric power and/or an electric signal to be transmitted from the first or second magnetic element 1A (1B) to the second or first magnetic element 1B (1A). As used herein, order numbers, "first" and "second" used to describe elements are only intended to distinguish "one" element from "another" element.

Either one of the first and second magnetic elements 1A and 1B, for example, the first magnetic element 1A, is fixed to the outer circumference of the shaft 5. The second magnetic element 1B is mounted so as to be rotatable relative to the shaft 5. The shaft 5 is mounted to one of a pair of housings (not shown) that rotate relative to each other, and the second magnetic element 1B is mounted to the other housing.

As shown in FIG. 2, the core 2A of the first magnetic element 1A of which the coil 3A is located radially inward of the coil 3B has an L cross-sectional shape including: a cylindrical portion (cylinder) 2aA located at the inner circumferential side of the coil 3A; and a flange portion (flange) 2bA extending radially outward from one end of the cylindrical portion 2aA. The core 2B of the second magnetic element 1B of which the coil 3B is located radially outward of the coil 3A has an L cross-sectional shape including: a cylindrical portion (cylinder) 2aB located on the outer circumference of the coil 3B; and a flange portion (flange) 2bB extending radially inward from one end in the axial direction, of the cylindrical portion 2aB. These flange portions 2bA and 2bB extend from the one ends of the cylindrical portions 2aA and 2aB at the inner side and the outer side, respectively, and these one ends are located at the opposite sides in the axial direction. The cross-sectional shapes of the respective cores 2A and 2B are L shapes that are rotated relative to each other by 180°.

The radially outer end of the flange portion 2bA in the core 2A of the first magnetic element 1A opposes the inner circumferential surface of the other end of the cylindrical portion 2aB of the core 2B in the second magnetic element 1B (that is, the end opposite to the end from which the flange portion 2bB extends) across a gap G1. The radially inner end of the flange portion 2bB in the core 2B of the second magnetic element 1B opposes the outer circumferential surface of the other end of the cylindrical portion 2aA in the core 2A of the first magnetic element 1A (that is, the end opposite to the end from which the flange portion 2bA extends) across a gap G2. The gaps G1 and G2 are filled with air in this embodiment, but may be filled with insulating materials, that is, an insulator such as a resin material may be interposed therebetween.

The cores 2A and 2B of the respective magnetic elements 1A and 1B are each a ferromagnetic substance and formed of a compaction-molded magnetic substance, an injection-molded magnetic substance, a laminated steel plate, or the like.

Specifically, the material of the compaction-molded magnetic substance can be a magnetic material such as iron powder; a pure iron-based soft magnetic material such as iron nitride powder; Fe—Si—Al alloy (sendust) powder; super sendust powder; Ni—Fe alloy (permalloy) powder; Co—Fe alloy powder; an iron group alloy-based soft magnetic material such as Fe—Si—B alloy powder; ferrite-based magnetic material; an amorphous-based magnetic material; and a microcrystal material.

Specifically, the injection-molded magnetic substance is obtained by blending a binding resin into the raw material powder for the compaction-molded magnetic substance and injection-molding the mixture. The magnetic powder is preferably amorphous metal powder, for example, since injection molding is easy, a shape is easily maintained after the injection molding, and the magnetic characteristics of a composite magnetic substance are excellent. The amorphous metal powder may include the above-described iron alloy powder, cobalt alloy powder, nickel alloy powder, or mixed alloy-based amorphous powder of these powders. The above-described insulating coating is formed on the surfaces of these amorphous metal powders.

The binding resin may be a thermoplastic resin, which can be injection-molded. The thermoplastic resin may be polyethylene or various other types of resin.

The coils 3A and 3B of the first and second magnetic elements 1A and 1B are obtained by winding coated conductive wires, formed of a rounded wire or the like, on the first and second bobbins 4A and 4B, respectively. In each of FIG. 1 to FIG. 3, the coated conductive wires are not shown, and the coils 3A and 3B are schematically represented. The bobbins 4A and 4B are each formed from a material having an insulating property and a good sliding property. The first and second bobbins 4A and 4B are each formed from a resin material such as polyphenylene sulfide (PPS).

The first bobbin 4A of the first magnetic element 1A includes a cylindrical portion (cylinder) 4aA and disk-shaped flange portions 4bA (cylinder) and 4cA extending radially outward from both ends in the axial direction of the cylindrical portion (cylinder) 4aA. The cylindrical portion 4aA and the flange portions 4bA and 4cA have the same inner diameter. The coated conductive wire of the coil 3A is wound on the outer circumference of the cylindrical portion 4aA over the area between the flange portions 4bA and 4cA. The coil 3A and the first bobbin 4A are fixed to the core 2A by fitting the inner circumferential surfaces of the cylindrical portion 4aA and the flange portions 4bA and 4cA of the first bobbin 4A to the outer circumferential surface of the cylindrical portion 2aA of the core 2A. The flange portion 4bA of the first bobbin 4A at one side is in contact with the flange portion 2bA of the core 2A.

The second bobbin 4B of the second magnetic element 1B includes a cylindrical portion 4aB and disk-shaped flange portions (flange) 4bB and 4cB extending radially outward from both ends in the axial direction of the cylindrical portion 4aB. The cylindrical portion 4aB and the flange portions 4bB and 4cB have the same inner diameter. The coated conductive wire of the coil 3B is wound on the outer circumference of the cylindrical portion 4aB over the area between the flange portions 4bB and 4cB. The coil 3B and the second bobbin 4B are fixed to the core 2B by fitting the outer circumferential surfaces of the flange portions 4bB and 4cB of the second bobbin 4B to the inner circumferential surface of the cylindrical portion 2aB of the core 2B. The flange portion 4cB of the second bobbin 4B at one side is in contact with the flange portion 2bB of the core 2B.

The positions of the first and second bobbins 4A and 4B are displaced in the axial direction relative to each other. That is, the flange portions 4bA and 4cA of the first bobbin 4A of the first magnetic element 1A are located at one side in the axial direction (at the upper side in the sheets of FIG. 1 and FIG. 2) with respect to the flange portions 4bB and 4cB of the second bobbin 4B of the second magnetic element 1B, respectively. The flange portion 4bA located at the one side in the axial direction, out of the two flange portions 4bA and 4cA of the first bobbin 4A, and the flange portion 4bB located at the one side in the axial direction, out of the two flange portions 4bB and 4cB of the second bobbin 4B, are slidably in contact with each other at contact surfaces thereof.

Figure 3:
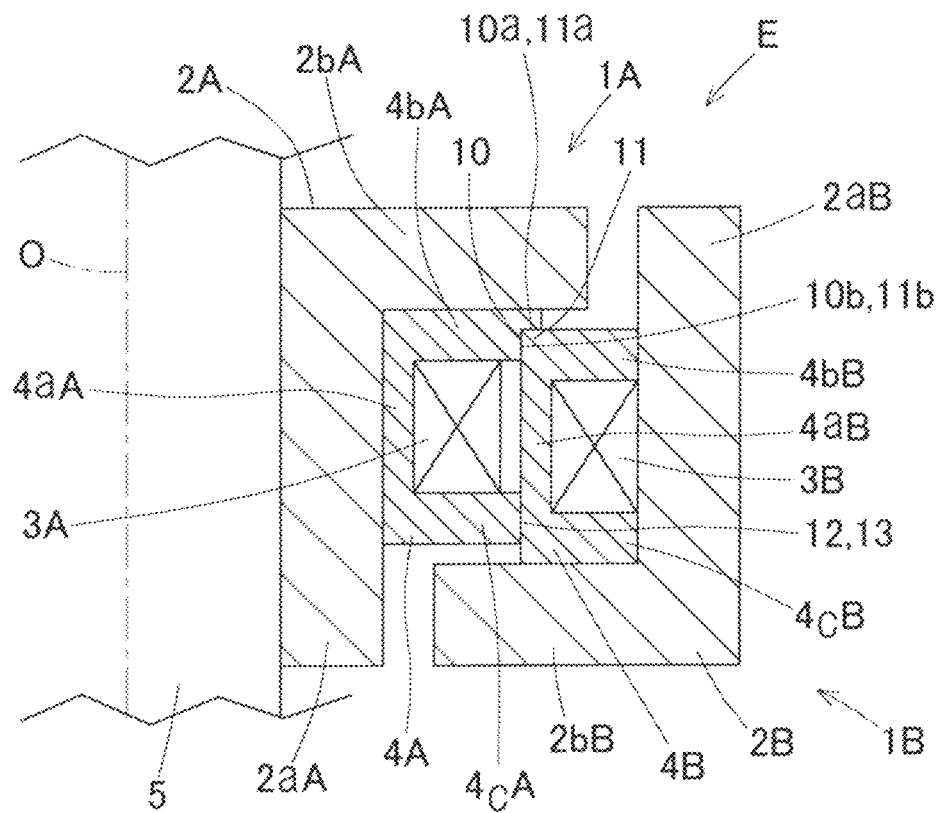
FIG. 3 is a partially enlarged view of FIG. 2.

Specifically, as shown in FIG. 3 which is a partially enlarged view of FIG. 2, an annular cut 10 that is open inwardly in the axial direction and has a rectangular cross-sectional shape is provided on the outer circumferential surface of the flange portion 4bA of the first bobbin 4A. Of the two flange portions 4bA and 4bB, the flange portion 4bA of the first bobbin 4A is located at the one side in the axial direction with respect to the flange portion 4bB of the second bobbin 4B. A corner portion 11 at the radially inner side of the flange portion 4bB of the second bobbin 4B is engaged with the annular cut 10. A surface 10a of the annular cut 10 that faces in the axial direction and a surface 11a of the corner portion 11 that faces in the axial direction function as the contact surfaces in the axial direction of the flange portions 4bA and 4bB, respectively.

As described above, the coils 3A and 3B of the first and second magnetic elements 1A and 1B are wound on the first and second bobbins 4A and 4B, respectively, and the flange portions 4bA and 4bB of the first and second bobbins 4A and 4B are slidably in contact with each other at the contact surfaces 10a and 11a in the axial direction. In this way, the first and second magnetic elements 1A and 1B can relatively rotate about the same axis O while the distance in the axial direction of the coils 3A and 3B and the cores 4A and 4B between the first and second magnetic elements 1A and 1B is maintained constant.

The first and second bobbins 4A and 4B are also slidably in contact with each other at contact surfaces thereof in the radial direction. In this embodiment, a surface 10b of the annular cut 10 of the first bobbin 4A that faces in the radial direction and a surface 11b of the corner portion 11 of the second bobbin 4B that faces in the radial direction function as the contact surfaces in the radial direction, and an outer circumferential surface 12 of the flange portion 4cA of the first bobbin 4A and an inner circumferential surface 13 of the cylindrical portion 4bB and the flange portion 4cB of the second bobbin 4B also function as the contact surfaces in the radial direction. Since the first and second bobbins 4A and 4B are slidably in contact with each other at the contact surfaces thereof in the radial direction as described above, the first and second magnetic elements 1A and 1B can relatively rotate about the same axis O while the distance in the radial direction of the cores 2A and 2B and the coils 3A and 3B between the first and second magnetic elements 1A and 1B is maintained constant.

As a configuration in which the flange portions of the first and second bobbins 4A and 4B are slidably in contact with each other at the contact surfaces thereof in the axial direction, the following configurations are adopted in electric transmission devices according to second to fifth embodiments shown in FIG. 4 to FIG. 7, in addition to the electric transmission device according to the first embodiment in FIG. 3.

Figure 4:
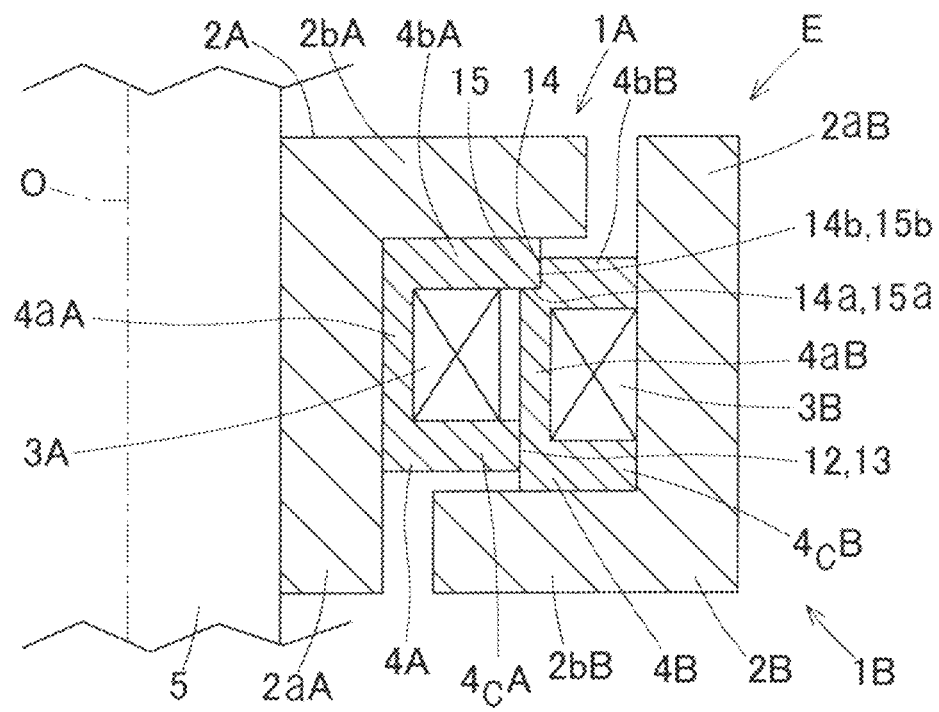
FIG. 4 is a partial longitudinal sectional view of an electric transmission device in relatively rotating parts according to a second embodiment of the present invention.

In the configuration of the electric transmission device according to the second embodiment shown in FIG. 4, in contrast to the configuration in FIG. 3, an annular cut 14 that is open outward in the axial direction and has a rectangular cross-sectional shape is provided on the inner circumferential surface of the flange portion 4bB of the second bobbin 4B. A corner portion 15 at the radially outer side of the flange portion 4bA of the first bobbin 4A is engaged with the annular cut 14. In this case, a surface 14a of the annular cut 14 that faces in the axial direction and a surface 15a of the corner portion 15 that faces in the axial direction function as the contact surfaces in the axial direction of the flange portions 4bB and 4bA, respectively. A surface 14b of the annular cut 14 that faces in the radial direction and a surface 15b of the corner portion 15 that faces in the radial direction function as the contact surfaces in the radial direction of the flange portions 4bB and 4bA, respectively.

Figure 5:
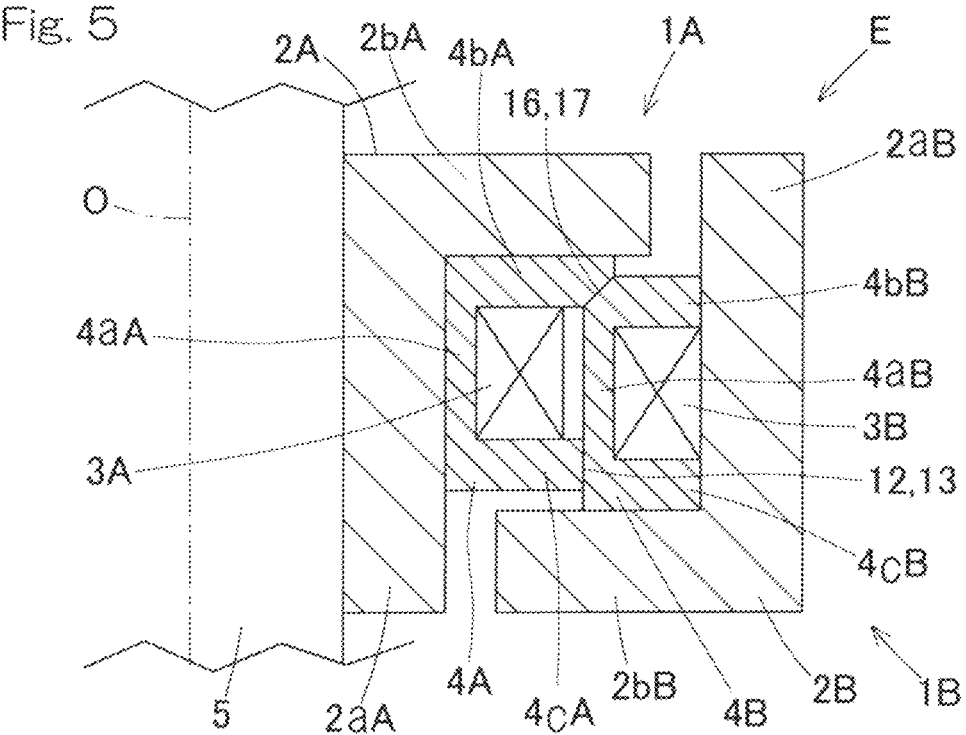
FIG. 5 is a partial longitudinal sectional view of an electric transmission device in relatively rotating parts according to a third embodiment of the present invention.

In the configuration of the electric transmission device according to the third embodiment shown in FIG. 5, inclined surfaces 16 and 17 that are inclined in the radial direction and are slidably in contact with each other are provided on the outer circumferential surface of the flange portion 4bA of the first bobbin 4A and the inner circumferential surface of the flange portion 4bB of the second bobbin 4B, respectively. In this case, the inclined surfaces 16 and 17 function as the contact surfaces in the axial direction of the flange portions 4bA and 4bB, respectively. The inclined surfaces 16 and 17 also function as the contact surfaces in the radial direction of the flange portions 4bA and 4bB, respectively.

Figure 6:
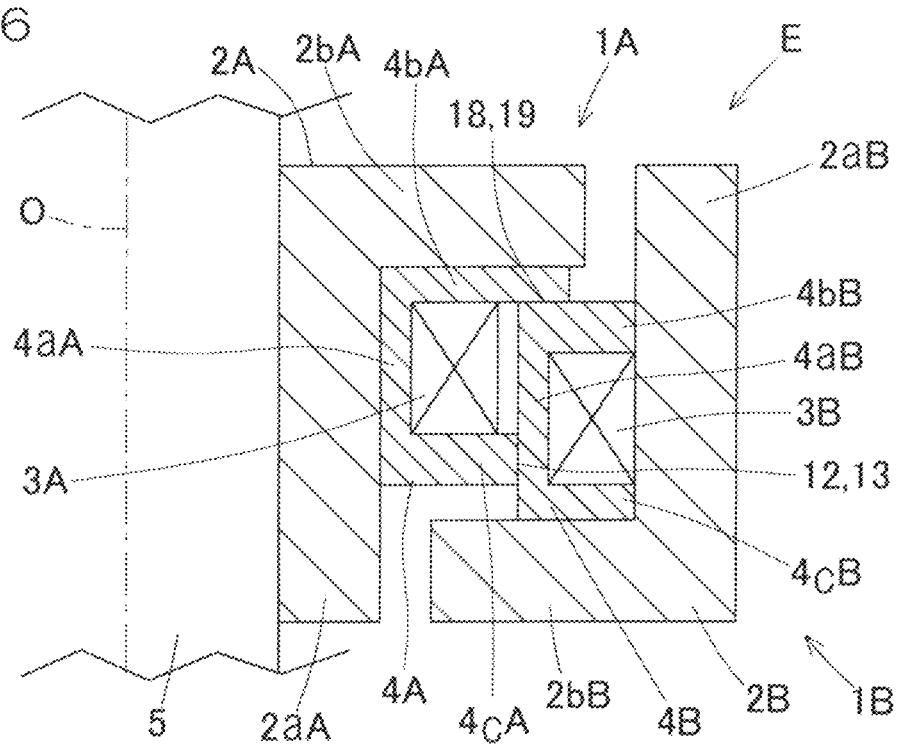
FIG. 6 is a partial longitudinal sectional view of an electric transmission device in relatively rotating parts according to a fourth embodiment of the present invention.

In the configuration of the electric transmission device according to the fourth embodiment shown in FIG. 6, the radially outer end of the flange portion 4bA of the first bobbin 4A projects at the radially outer side with respect to the position of the radially inner end of the flange portion 4bB of the second bobbin 4B, and an inward end surface (a surface facing in the axial direction) 18 of this projection portion is slidably in contact with an outward end surface (a surface facing in the axial direction) 19 of the flange portion 4bB. In this case, the inward end surface 18 and the outward end surface 19 function as the contact surfaces in the axial direction of the flange portions 4bA and 4bB, respectively.

Figure 7:
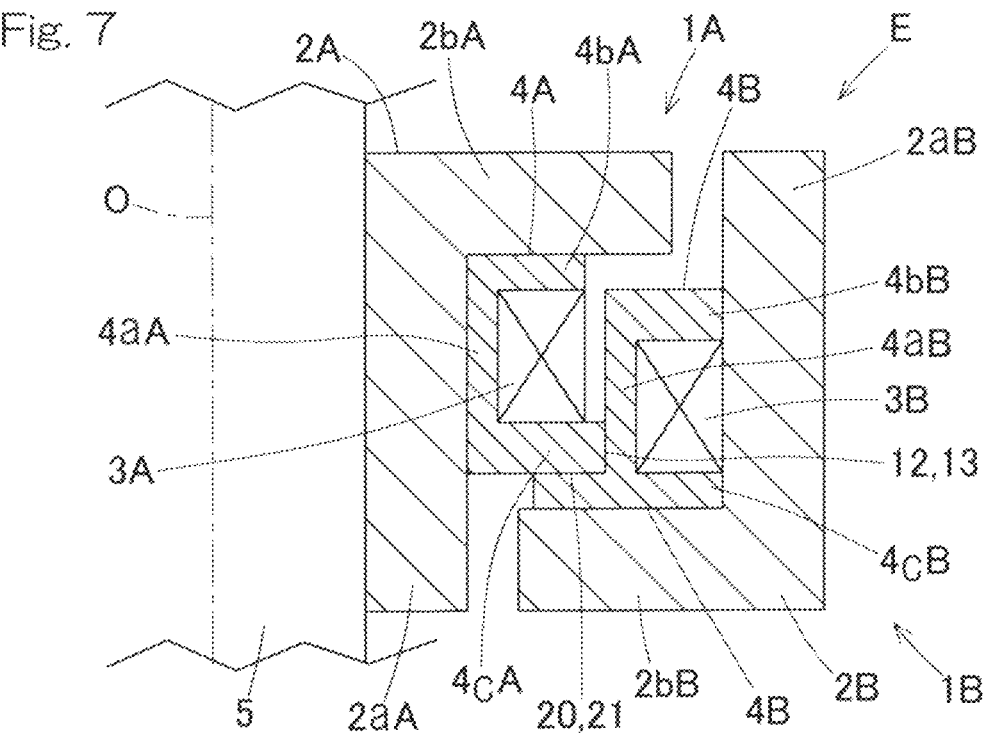
FIG. 7 is a partial longitudinal sectional view of an electric transmission device in relatively rotating parts according to a fifth embodiment of the present invention.

In the configuration of the electric transmission device according to the fifth embodiment shown in FIG. 7, in contrast to the configuration in FIG. 6, the radially inner end of the flange portion 4cB of the second bobbin 4B projects at the radially inner side with respect to the position of the radially outer end of the flange portion 4cA of the first bobbin 4A, and an inward end surface (a surface facing in the axial direction) 20 of this projection portion is slidably in contact with an outward end surface (a surface facing in the axial direction) 21 of the flange portion 4cA. In this case, the inward end surface 20 and the outward end surface 21 function as the contact surfaces in the axial direction of the flange portions 4cB and 4cA, respectively.

In each of the configurations in FIG. 4 to FIG. 7, similar to the configuration in FIG. 3, the first and second magnetic elements 1A and 1B can relatively rotate about the same axis O while the distance in the axial direction of the coils 3A and 3B and the cores 4A and 4B between the first and second magnetic elements 1A and 1B is maintained constant. The configurations other than the above-described configurations of the electric transmission devices according to the second to fifth embodiments are the same as in the electric transmission device according to the first embodiment.

According to the configuration of the electric transmission device E, connecting either one of the first and second magnetic elements 1A and 1B, for example, the coil 3A (3B) of the first magnetic element 1A (1B), to a circuit associated with a power feeder and connecting the coil 3B (3A) of the second magnetic element 1B (1A) to a circuit associated with a power receiver enables electric power or an electric signal to be transmitted from the power feeder to the power receiver by means of the two coils 3A and 3B, which are magnetically coupled to each other. Since one of the two coils 3A and 3B is located at the inner side of the other coil in the radial direction, the factor of the magnetic coupling between both coils 3A and 3B is increased, thereby improving the efficiency of transmission of electric power or an electric signal. Thus, the electric transmission device E is prevented from increasing in size.

As described above, since the bobbins 4A and 4B of the first and second magnetic elements 1A and 1B are slidably in contact with each other, the first and second magnetic elements 1A and 1B can relatively rotate about the same axis O while the distance in the axial direction and the distance in the radial direction of the cores 2A and 2B and the coils 3A and 3B between the first and second magnetic elements 1A and 1B are maintained constant. In this way, during assembling or operation, damage to the cores 2A and 2B and the coils 3A and 3B of the first and second magnetic elements 1A and 1B due to contact therebetween can be avoided. In addition, the positions of the cores 2A and 2B and the coils 3A and 3B between the respective magnetic elements that are kept fixed in the axial direction stabilizes the magnetic characteristics.

Winding the conductive wires of the coils 3A and 3B of the first and second magnetic elements 1A and 1B on the respective outer circumferences of the first and second bobbins 4A and 4B which are concentric with the axis O facilitates work for winding the conductive wires on the bobbins 4A and 4B. Positioning the cores 2A and 2B and the coils 3A and 3B by the bobbins 4A and 4B also facilitates assembling the electric transmission device E.

Figure 8:
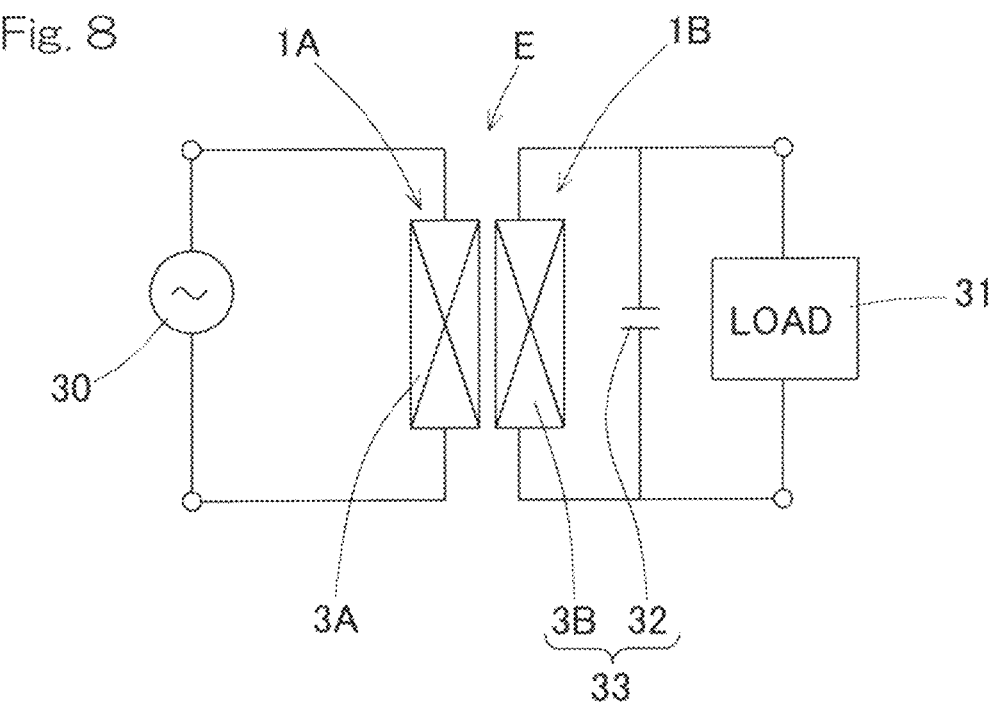
FIG. 8 is an electric circuit diagram of the electric transmission device.

FIG. 8 shows an example of an electric circuit in which the electric transmission device E is used for feeding electric power. Either one of the first and second magnetic elements 1A and 1B, for example, the coil 3A of the first magnetic element 1A, is associated with a power feeder (primary side) and is connected to an AC power source 30. The coil 3B of the second magnetic element 1B is associated with a power receiver (secondary side) and is connected to a load 31 such as a motor. A capacitor 32 is connected in parallel to the coil 3B associated with the power receiver. The capacitor 32 and a leakage inductance due to a leakage magnetic flux generated at the coil 3B associated with the power receiver form a resonance circuit 33. An electric signal source (not shown) may be provided instead of the AC power source 30 or so as to be superimposed on an AC voltage outputted from the AC power source 30, and a demodulating circuit (not shown) may be provided instead of the load 31 or together with the load 31, whereby an electric signal can be transmitted. The numbers of turns of the coils 3A and 3B associated with the respective power feeder and the power receiver may be made different from each other, thereby providing a boost (step-up) or buck (step-down) function.

Figure 9:
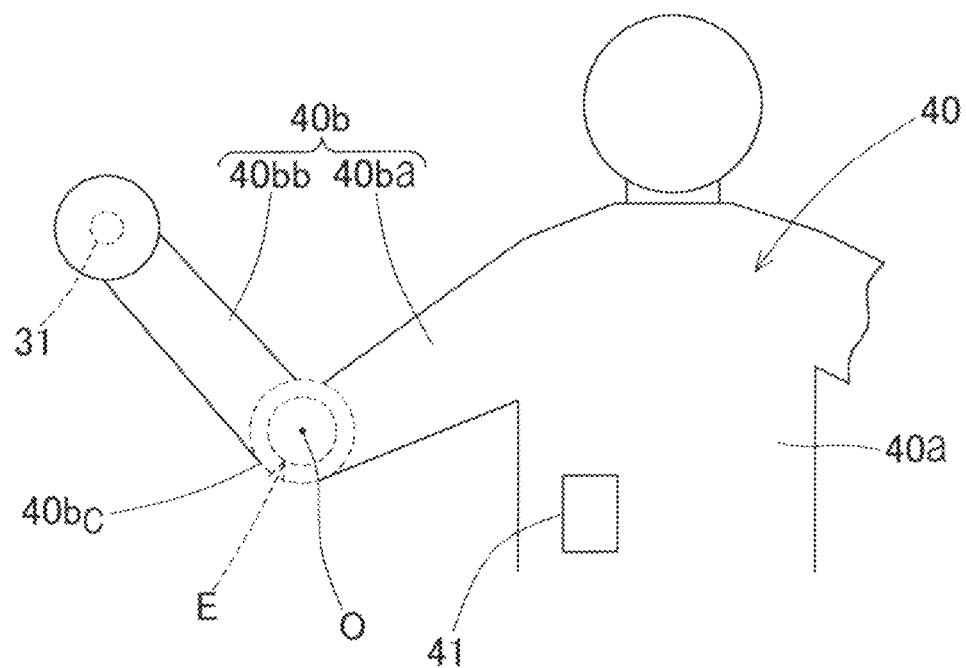
FIG. 9 illustrates an example of a power assist suit employing the electric transmission device.

FIG. 9 shows an example in which a mechanical apparatus equipped with the electric transmission device E in relatively rotating parts is a power assist suit 40. The power assist suit 40 has: a trunk portion 40a that is worn on the trunk of a human body; and arm portions 40b that extend from the trunk portion 40a. Each of the arm portions 40b has an upper arm portion 40ba and a forearm portion 40bb. The upper arm portion 40ba and the forearm portion 40bb are components configured to be relatively bent. A joint part 40ac serving as an elbow that is a relatively bending part between the upper arm and forearm portions 40ba and 40bb is a joint part with one degree of freedom that is rotatable about an axis O. A power source 41 is provided to the trunk portion 40a. The load 31 such as an electric motor for driving a wrist or a hand is provided at the distal end of the arm portion 40b. Wires (not shown) extending from the power source 41 and connected to the load 31 are separated at the joint part 40ac. These separated wires are connected to the electric transmission device E described in each of the above embodiments, so that power and/or an electric signal is transmitted via the electric transmission device E.

For the power assist suit 40, reliability in transmission of electric power or an electric signal and a reduction in the size of the electric transmission device at the joint part are strongly desired. Meanwhile, the electric transmission device according to each embodiment achieves reliability in transmission and reduces its size, and thus the electric transmission device can sufficiently meet these desires.

Hereinafter, an electric transmission device according to a sixth embodiment of the present invention will be described. It should be noted that in this embodiment, the description of bobbins of magnetic elements is omitted, and the configuration of the bobbins in any of the electric transmission devices according to the first to fifth embodiments described above is adopted in the electric transmission device according to the sixth embodiment.

Figure 10:
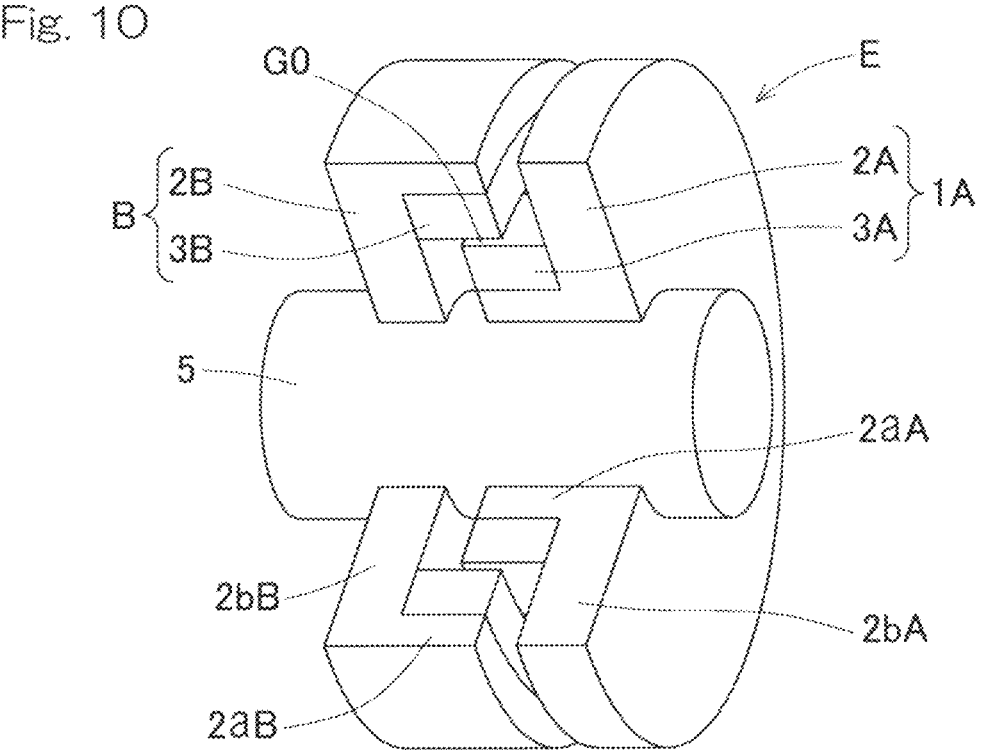
FIG. 10 is a partially cutaway perspective view of an electric transmission device in relatively rotating parts according to a sixth embodiment of the present invention.
Figure 11:
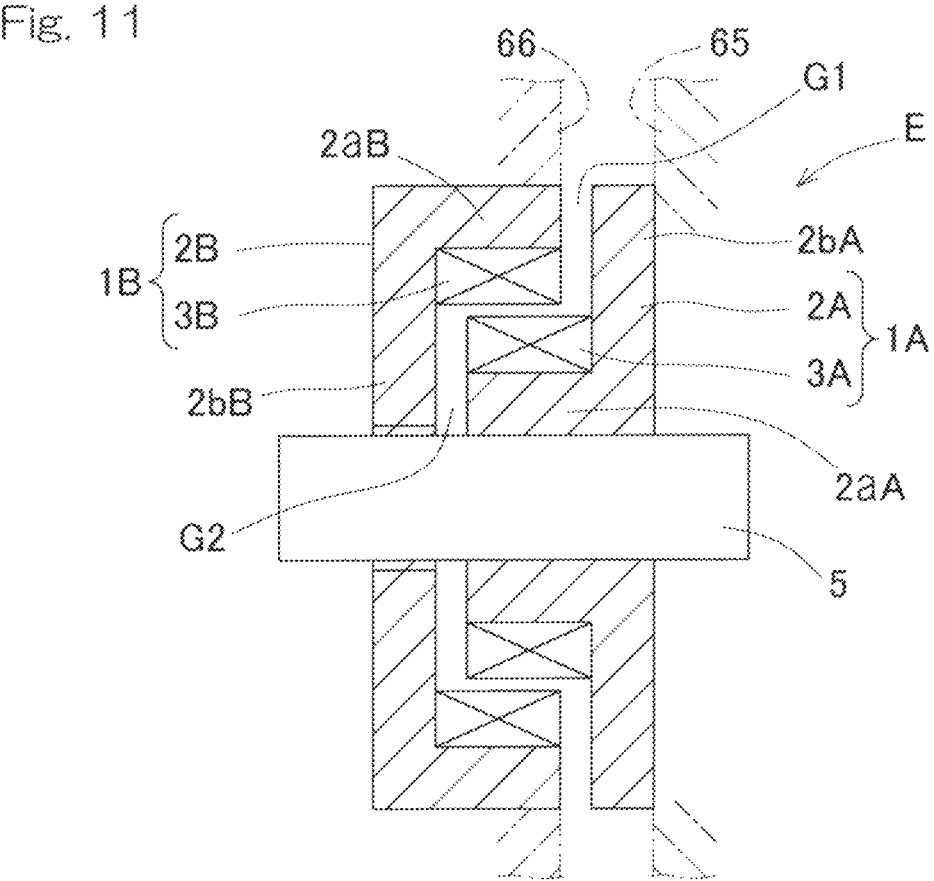
FIG. 11 is a longitudinal sectional view of the electric transmission device in FIG. 10.
Figure 12:
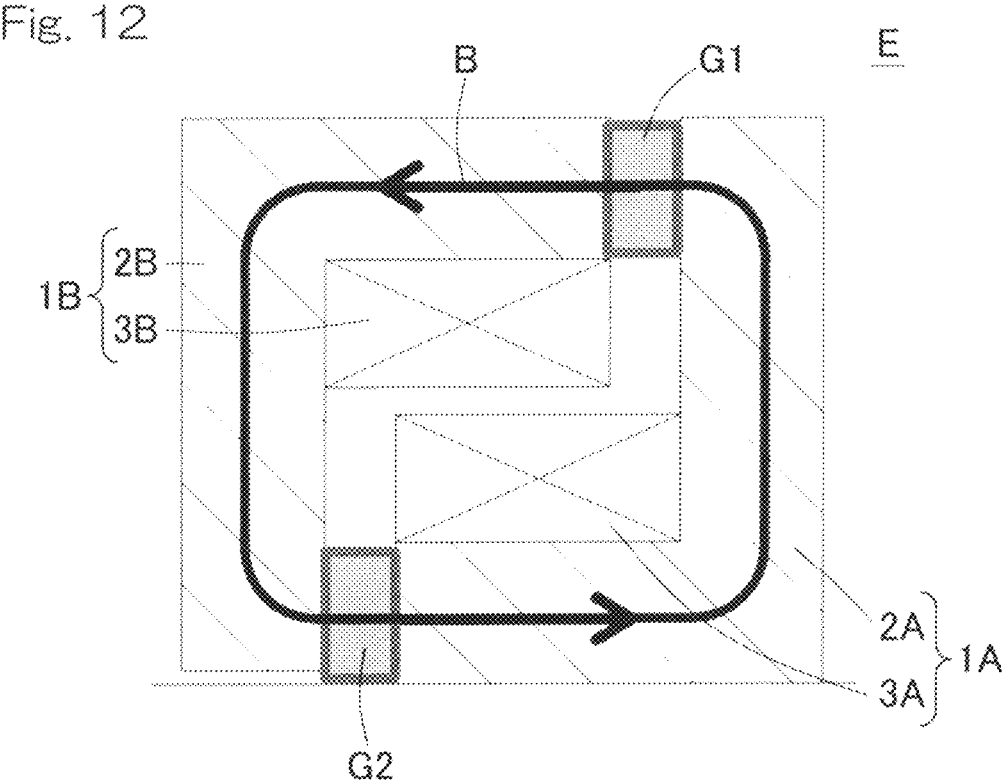
FIG. 12 illustrates flow of a magnetic flux of the transmission device in FIG. 10.

The electric transmission device according to the sixth embodiment of the present invention will be described with reference to FIG. 10 to FIG. 12. The electric transmission device E in relatively rotating parts includes the same components as those in the electric transmission devices E described in the first to fifth embodiments, and the description of the same components is partially omitted below.

The electric transmission device E includes first and second magnetic elements 1A and 1B. Of these magnetic elements 1A and 1B, the first magnetic element 1A has a projection shape, and the second magnetic element 1B has a recess shape, so that the magnetic elements 1A and 1B conform to each other. Specifically, the core 2A of the first magnetic element 1A of which the coil 3A is located at the inner side in the radial direction has an L cross-sectional shape including: a cylindrical portion 2aA located on the inner circumference of the coil 3A; and a flange portion 2bA extending radially outward from one end of the cylindrical portion 2aA and having a radially outer end that has a larger diameter than the coil 3B of the second magnetic element 1B. The core 2A and the coil 3A form the first magnetic element 1A having the projection shape of a pot shape.

The core 2B of the second magnetic element 1B has an L cross-sectional shape including: a cylindrical portion 2aB, at the outer circumferential side, located on the outer circumference of the coil 3B of the magnetic element 1B and having an end that has an end surface opposing the flange portion 2bA of the core 2A of the first magnetic element 1A across a gap G1; and a flange portion 2bB extending radially inward from the other end of the cylindrical portion 2aB and having a radially inner end opposing the end surface of the cylindrical portion 2aA of the core 2A of the first magnetic element 1A across a gap G2.

In a reference example that is not included in the scope of the present invention, the coils 3A and 3B of the first and second magnetic elements 1A and 1B may each be a rectangular conductive wire wound in a single layer without a bobbin.

According to the electric transmission device E having this configuration, in the first and second magnetic elements 1A and 1B, the coils 3A and 3B are located at the inner side and the outer side in the radial direction, respectively, and thus the factor of the magnetic coupling therebetween is increased, thereby improving the efficiency of transmission of electric power or an electric signal. Thus, the electric transmission device is prevented from increasing in size. The magnetic coupling also prevents breaking of wire or an environmental problem. A magnetic flux B of the coils 3A, 3B passes as indicated by an arrow B in FIG. 12. As described above, the gaps G1 and G2 are filled with air or insulating materials that traverse so as to be perpendicular to a magnetic path.

In the electric transmission device E, of the first and second magnetic elements 1A and 1B, the first magnetic element 1A has a projection shape, and the second magnetic element 1B has a recess shape. Thus, the positions of the gaps G1 and G2 are not close to the coils, where a leakage magnetic flux is easily absorbed, and thus the inductance value is improved. In addition, one of the coils 3A and 3B associated with the respective power feeder and power receiver is located radially inward of the other coil, which increases the coupling factor therebetween and reduces a leakage magnetic flux. In this way, the inductance value is improved, and the core size can be reduced further. Moreover, magnetic elements 1A and 1B, to be arranged at opposite sides, have a projection shape and a recess shape, respectively, and thus are easily distinguished, so that erroneous assembling can be prevented.

The efficiency can be improved by the resonance circuit 33 (FIG. 8) formed by: a leakage inductance generated by a magnetic flux leaking to air, that is, the gaps G1 and G2; and the capacitor 32 (FIG. 8) connected to the coil 3B of the magnetic element 1B associated with the power receiver.

As described above, with the electric transmission device E of this embodiment, the following advantageous effects are achieved.

(1) A cable used at a joint part for transmitting electric power or a signal would be broken due to the stress that is repeatedly caused by bending. The electric transmission device E in which the cores are relatively operable enables electric power or a signal to be transmitted without a wire, which might be broken.

(2) In the electric transmission device E, a pot-shaped inductor is made up of the second magnetic element 1B having a recess shape and the first magnetic element 1A having a projection shape, and thus a leakage magnetic flux is inhibited from being absorbed by the coils. In addition, since the coil 3A is disposed radially inward of the other coil 3B, the coupling coefficient is increased.

(3) The efficiency can be improved by the resonance circuit 33 formed by the capacitor 32 and the leakage inductance of a leakage magnetic flux at gaps G1 and G2, so that the electric transmission device is prevented from increasing in size.

Figure 13:
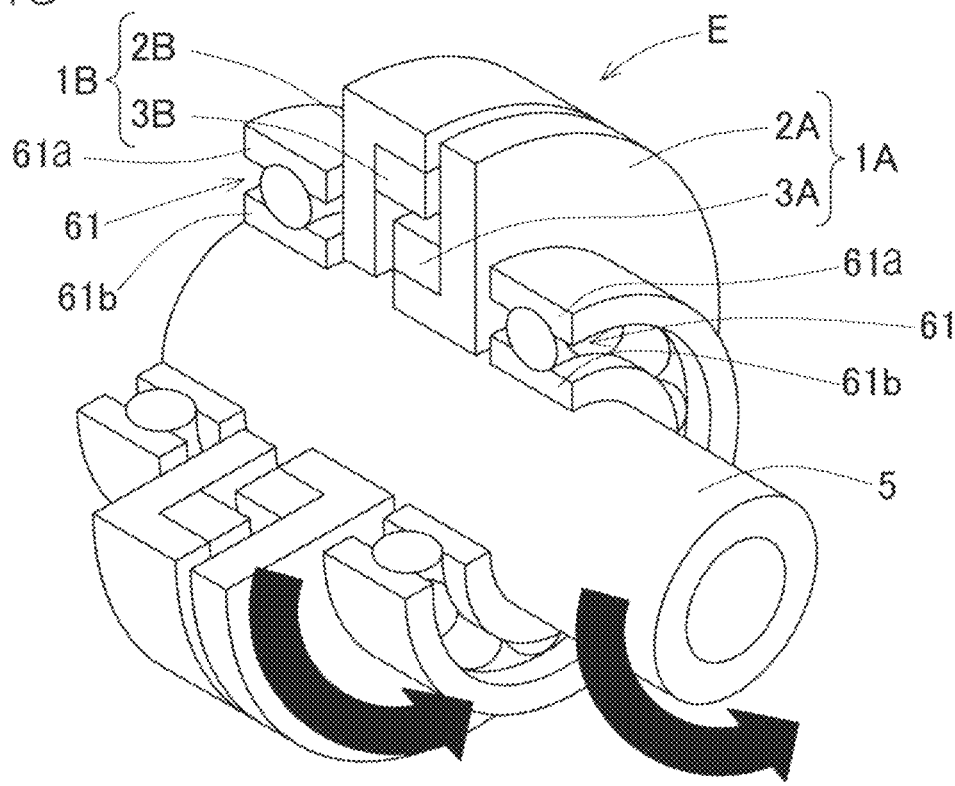
FIG. 13 is a partially cutaway perspective view of an example in which the electric transmission device in FIG. 10 is equipped with bearings.

FIG. 13 shows an example in which the electric transmission device E in relatively rotating parts according to the sixth embodiment is mounted to housings 65 and 66 (FIG. 11) using a pair of bearings 61, 61. Each bearing 61 is a radial bearing, and, specifically, may be a deep groove ball bearing. In this example, an outer ring 61a of each bearing 61 and the second magnetic element 1B, having a recess shape are fixed to the housings 65 and 66 (FIG. 11), and an inner ring 61b of each bearing 61 and the first magnetic element 1A, having a projection shape are fixed to the shaft 5 such as a support shaft. In the case of feeding power from the housing side, power can be fed to a device fixed to the shaft 5, via the electric transmission device E in a non-contact manner.

Figure 14:
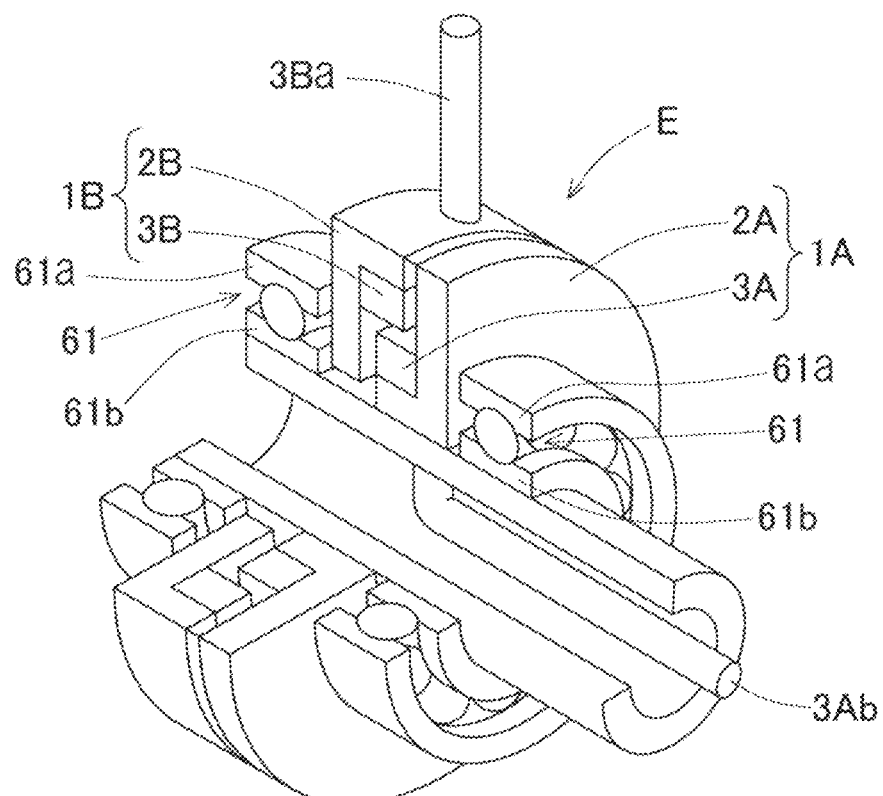
FIG. 14 is a partially cutaway perspective view of an example in which lead wires are added to the electric transmission device in FIG. 13.

FIG. 14 shows an example in which extended cables (signal lines) are further added to the electric transmission device E in FIG. 13. In this example, in the second magnetic element 1B, having a recess shape, a lead wire 3Ba is extended through a radially outer portion of the core 2B. A lead wire 3Ba may be extended through an end surface of the core 2B. In the first magnetic element 1A having a projection shape and fixed to the shaft 5, a lead wire 3Ab is extended from the coil 3A through a radially inner hole of the shaft 5 that is hollow. In this way, the lead wires 3Ba and 3Ab, which are electric power cables and/or signal lines, can be extended without interfering with a member at the housing side. Similar to the electric transmission device E according to the sixth embodiment, each of the electric transmission devices E according to the first to fifth embodiments may be fixed to a device via bearings as shown in FIG. 13 and FIG. 14.

The configuration of the cores in the first to fifth embodiments of the present invention will be described in detail with reference to FIG. 15. Of the first and second magnetic elements 1A and 1B, the core 2A of the first magnetic element 1A of which the coil 3A is located at the radially inner side with respect to the coil 3B has an L cross-sectional shape including: the cylindrical portion 2aA located at the inner circumferential side of the coil 3A of the first magnetic element 1A; and the flange portion 2bA extending radially outward from one end of the cylindrical portion 2aA and having a radially outer end opposing the inner circumferential surface of the core end portion of the second magnetic element 1B across a gap G3.

The core 2B of the second magnetic element 1B includes: the cylindrical portion 2aB located on the outer circumference of the coil 3B of the magnetic element 1B and having one end portion that has an inner circumferential surface opposing the flange portion 2bA of the core 2A of the first magnetic element 1A; and the flange portion 2bB extending radially inward from the other end of the cylindrical portion 2aB and having a radially inner end that has a smaller diameter than the coil 3B of the second magnetic element 1B.

In FIG. 15, the description of the bobbins of the magnetic elements is omitted. However, in the reference example that is not included in the scope of the present invention, the coils 3A and 3B of the first and second magnetic elements 1A and 1B are provided without bobbins. These coils 3A and 3B are located at the inner side and the outer side in the radial direction, respectively, with a gap G0 (FIG. 10) interposed therebetween, and are magnetically coupled to each other.

In the case of this configuration as well, the positions of the gaps are not close to the coils, where a leakage magnetic flux is easily absorbed, and thus the inductance value is improved. In addition, one of the coils 3A and 3B associated with the respective power feeder and power receiver is located radially inward of the other coil, which increases the coupling factor therebetween and reduces a leakage magnetic flux. In this way, the inductance value is improved, and the core size can be reduced further. Moreover, magnetic elements 1A and 1B, to be arranged at opposite sides, have a projection shape and a recess shape, respectively, and thus are easily distinguished, so that erroneous assembling can be prevented.

Figure 17:
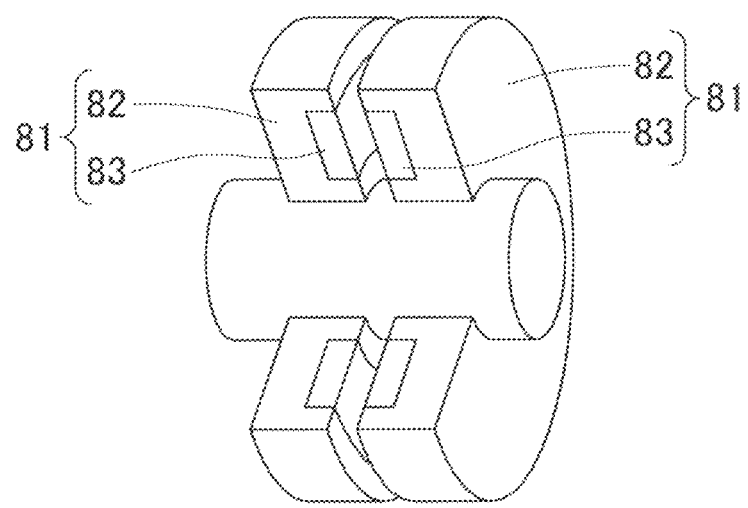
FIG. 17 is a partially cutaway perspective view of a conventional electric transmission device.
Figure 18:
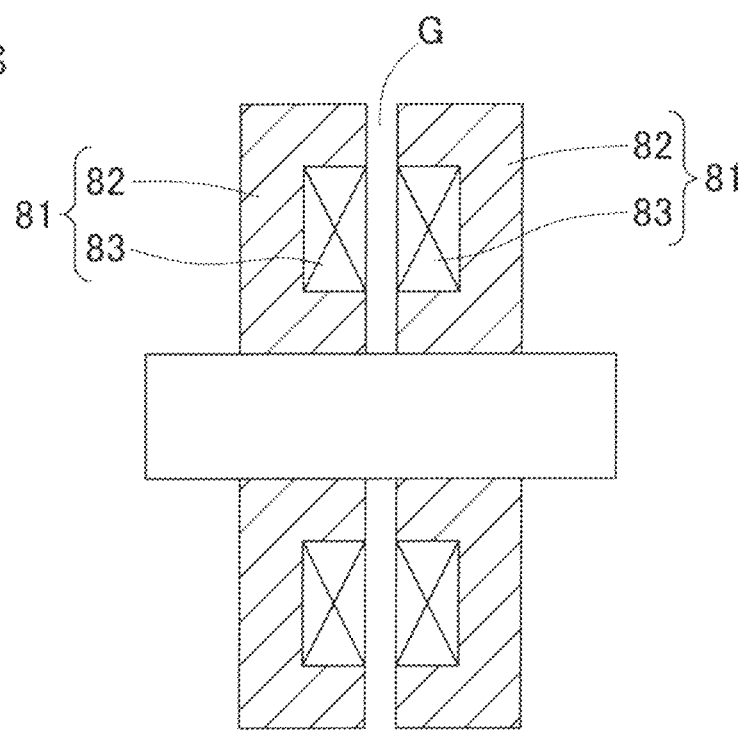
FIG. 18 is a longitudinal sectional view of the electric transmission device in FIG. 17.

Next, the electric transmission devices according to the first to sixth embodiments are compared to a conventional electric transmission device shown in FIGS. 17 and 18. As shown in FIGS. 17 and 18, in the conventional electric transmission device, magnetic elements 81, 81 each having a basic pot-shaped core 82 oppose each other. The positions of gaps are close to coils 83, 83, where a leakage magnetic flux is easily absorbed. The magnetic coupling is achieved between the coils. Each magnetic element 81 includes the core 82 and the coil 83, and the coils 83 and the cores 82 of both magnetic elements 81, 81 oppose each other across a gap G.

Figure 16A:
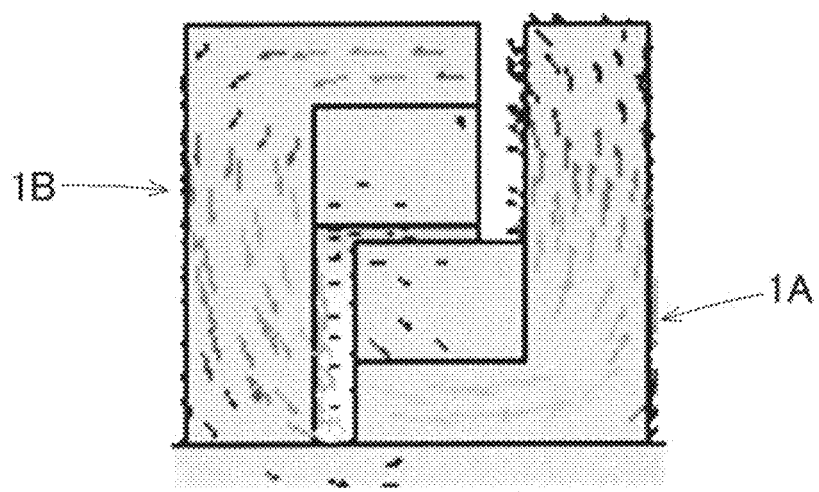
FIG. 16A illustrates an explanatory drawing showing flow of a magnetic flux of the electric transmission device according to the sixth embodiment.
Figure 16B:
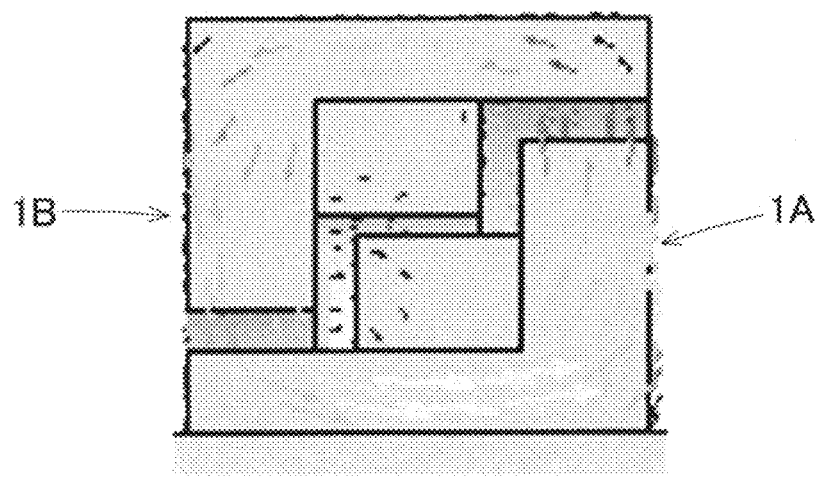
FIG. 16B illustrates an explanatory drawing showing a magnetic flux of the electric transmission device according to the first to fifth embodiments.
Figure 16C:
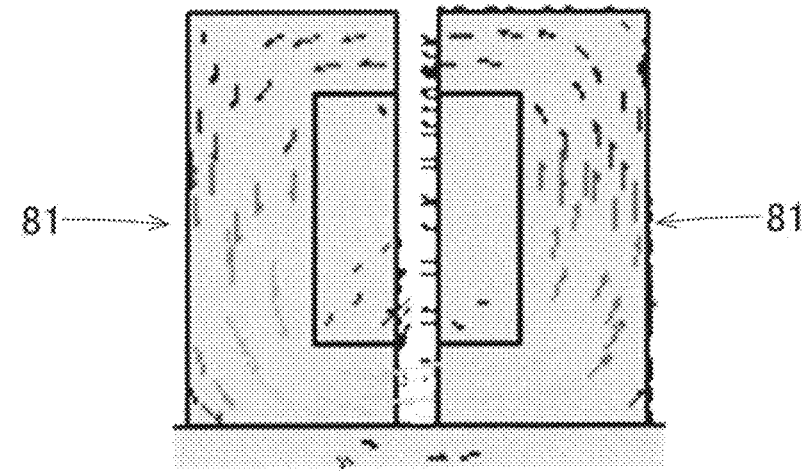
FIG. 16C illustrates an explanatory drawing showing a magnetic flux of an electric transmission device according to a conventional art example.

FIGS. 16A to 16C show magnetic flux flows in the sixth embodiment, the first to fifth embodiments, and the conventional art example in FIGS. 17 and 18, respectively. As seen from these drawings, in each embodiment described above, compared to the conventional art example, the inductance value is improved since the positions of the gaps are not close to the coils, where a leakage magnetic flux is easily absorbed. Although the bobbins are not shown in FIGS. 16A to 16C, presence/absence of the bobbins does not influence a relative result of the above-described magnetic flux flows.

Although the modes for carrying out the present invention have been described on the basis of the embodiments, the embodiments disclosed herein are illustrative in all aspects and not restrictive. The scope of the present invention is indicated by the claims, rather than by the above description, and is intended to include any modifications within the scope and meaning equivalent to the claims.

REFERENCE NUMERALS 1A, 1B . . . magnetic element
2A, 2B . . . core
3A, 3B . . . coil
4A, 4B . . . bobbin
4aA, 4aB . . . bobbin cylinder
4bA, 4bB . . . bobbin flange
4cA, 4cB . . . bobbin flange
10a, 11a, 14a, 15a, 16, 17 . . . contact surface in axial direction
E . . . electric transmission device
O . . . axis

What is claimed is:

1. An electric transmission device comprising:
a pair of first and second magnetic elements relatively rotatable about the same axis, wherein
the first and second magnetic elements, each comprises a core and a coil having a conductive wire, one of the coils of the first and second magnetic elements being located at an inner side of the other coil in a radial direction with respect to the axis, the coils being configured to be magnetically coupled to each other, the magnetic coupling enabling electric power and/or an electric signal to be transmitted,
the first and second magnetic elements further comprise respective first and second bobbins, the first and second bobbins being located so as to be concentric with the axis,
the first and second bobbins each comprises a bobbin cylinder and a disk-shaped bobbin flange, the bobbin cylinder extending in an axial direction that is a direction of the axis and having an outer circumference on which the conductive wire of the corresponding coil is wound, the disk-shaped bobbin flange extending radially outward from at least one end portion of the bobbin cylinder, and
the bobbin flanges of the first and second bobbins are slidably in contact with each other at contact surfaces in the axial direction of the bobbin flanges, the contact surfaces opposing each other in the axial direction.

2. The electric transmission device as claimed in claim 1, wherein
at both ends or one end in the axial direction of the first and second bobbins, a position of the bobbin flange of the first bobbin and a position of the bobbin flange of the second bobbin are displaced relative to each other in the axial direction, and
at at least either one of both ends or the one end in the axial direction of the first and second bobbins, an annular cut is formed on a circumferential surface of the bobbin flange located at an outer side in the axial direction, a corner portion in the radial direction of the bobbin flange located at an inner side in the axial direction is engaged with the annular cut, and a surface of the annular cut that faces in the axial direction and a surface of the corner portion that faces in the axial direction function as the respective contact surfaces in the axial direction.

3. The electric transmission device as claimed in claim 1, wherein
at both ends or one end in the axial direction of the first and second bobbins, a position of the bobbin flange of the first bobbin and a position of the bobbin flange of the second bobbin are displaced relative to each other in the axial direction, and
at at least either one of both ends or the one end in the axial direction of the first and second bobbins, an annular cut is formed on a circumferential surface of the bobbin flange located at an inner side in the axial direction, a corner portion in the radial direction of the bobbin flange located at an outer side in the axial direction is engaged with the annular cut, and a surface of the annular cut that faces in the axial direction and a surface of the corner portion that faces in the axial direction function as the respective contact surfaces in the axial direction.

4. The electric transmission device as claimed in claim 1, wherein
at both ends or one end in the axial direction of the first and second bobbins, a position of the bobbin flange of the first bobbin and a position of the bobbin flange of the second bobbin are displaced relative to each other in the axial direction, and
at at least either one of both ends or the one end in the axial direction of the first and second bobbins, inclined surfaces that are inclined toward the radial direction and slidably in contact with each other are provided on a circumferential surface of the bobbin flange located at an outer side in the axial direction and a circumferential surface of the bobbin flange located at an inner side in the axial direction, respectively, and the inclined surfaces function as the respective contact surfaces in the axial direction.

5. The electric transmission device as claimed in claim 1, wherein
at both ends or one end in the axial direction of the first and second bobbins, a position of the bobbin flange of the first bobbin and a position of the bobbin flange of the second bobbin are displaced relative to each other in the axial direction, and
at at least either one of both ends or the one end in the axial direction of the first and second bobbins, an inward end surface of the bobbin flange located at an outer side in the axial direction is slidably in contact with an outward end surface of the bobbin flange located at an inner side in the axial direction, and the inward end surface and the outward end surface function as the respective contact surfaces in the axial direction.

6. The electric transmission device as claimed in claim 1, wherein the first bobbin and the second bobbin each has a contact surface in the radial direction, the contact surfaces opposing each other in the radial direction and being slidably in contact with each other.

7. The electric transmission device as claimed in claim 1, wherein
the coil of the first magnetic element is located at the inner side of the other coil in the radial direction, the core of the first magnetic element having an L cross-sectional shape, the core of the first magnetic element including a first core cylinder and a first core flange, the first core cylinder being located on an inner side of an inner circumference of the coil of the first magnetic element, the first core flange extending radially outward from an end portion of the first core cylinder, the first core flange having a radially outer end that has a larger diameter than the coil of the second magnetic element, and
the core of the second magnetic element has a L cross-sectional shape that is symmetrical to the core of the first magnetic element, the core of the second magnetic element including a second core cylinder and a second core flange, the second core cylinder being located on an outer side of an outer circumference of the coil of the second magnetic element, the second core cylinder having an end portion that has an end surface opposing the first core flange of the core of the first magnetic element across a first gap, the second core flange extending radially inward from the other end portion of the second core cylinder, the second core flange having a radially inner end portion opposing an end surface of the first core cylinder of the core of the first magnetic element across a second gap.

8. The electric transmission device as claimed in claim 1, wherein
the coil of the first magnetic element is located at the inner side of the other coil in the radial direction, the core of the first magnetic element having an L cross-sectional shape, the core of the first magnetic element including a first core cylinder and a first core flange, the first core cylinder being located on an inner side of an inner circumference of the coil of the first magnetic element, the first core flange extending radially outward from an end portion of the first core cylinder, the first core flange having a radially outer end portion opposing an inner circumferential surface of a core end portion of the second magnetic element across a first gap, and
the core of the second magnetic element has a L cross-sectional shape that is symmetrical to the core of the first magnetic element, the core of the second magnetic element including a second core cylinder and a second core flange, the second core cylinder being located on an outer side of an outer circumference of the coil of the second magnetic element, the second core cylinder having an end portion that has an inner circumferential surface opposing the first core flange of the core of the first magnetic element, the second core flange extending radially inward from the other end portion of the second core cylinder, the second core flange having a radially inner end that has a smaller diameter than the coil of the second magnetic element.

9. The electric transmission device as claimed in claim 1, wherein a capacitor and a leakage inductance of a leakage magnetic flux at a gap between the first and second magnetic elements form a resonance circuit, the resonance circuit including a coil associated with a power receiver implemented at the first or second magnetic element and a capacitor connected to the coil.

10. The electric transmission device as claimed in claim 1, wherein the first magnetic element is fixed to a shaft, and the second magnetic element is mounted to the shaft through a radial rolling bearing.

11. The electric transmission device as claimed in claim 1, wherein the first magnetic element is mounted on one component in a pair of relatively bending components and the second magnetic element is mounted on the other component in the pair, the pair forming a joint of a mechanical apparatus.

12. The electric transmission device as claimed in claim 11, wherein the mechanical apparatus is a power assist suit that is worn on a human body and assists movement of an arm, a leg, a hand, or a foot of the human body with a drive source.

* * * * *

UNITED STATES PATENT AND TRADEMARK OFFICE
CERTIFICATE OF CORRECTION

PATENT NO. : 11,456,115 B2
APPLICATION NO. : 16/180232
DATED : September 27, 2022
INVENTOR(S) : Kayo Sakai et al.

It is certified that error appears in the above-identified patent and that said Letters Patent is hereby corrected as shown below:

On the Title Page

Item (71), Column 1, Lines 1-3, delete "Kayo Sakai, Kuwana (JP); Eiichirou Shimazu, Kuwana (JP); Shougo Kanbe, Kuwana (JP)" and insert --NTN CORPORATION, Osaka (JP)--.

Column 2, Line 10 of item (57), delete "dis-shaped" and insert --disk-shaped--.

Signed and Sealed this
Twenty-seventh Day of February, 2024

Katherine Kelly Vidal
*Director of the United States Patent and Trademark Office*